United States Patent
Koseoglu et al.

(10) Patent No.: US 10,942,160 B2
(45) Date of Patent: Mar. 9, 2021

(54) CHARACTERIZATION OF CRUDE OIL AND ITS FRACTIONS BY FOURIER TRANSFORM INFRARED (FTIR) SPECTROSCOPY ANALYSIS

(71) Applicant: Saudi Arabian Oil Company, Dhahran (SA)

(72) Inventors: Omer Refa Koseoglu, Dhahran (SA); Adnan Al-Hajji, Dhahran (SA); Amer A. Al-Tuwailib, Dhahran (SA)

(73) Assignee: SAUDI ARABIAN OIL COMPANY, Dhahran (SA)

( * ) Notice: Subject to any disclaimer, the term of this patent is extended or adjusted under 35 U.S.C. 154(b) by 0 days.

(21) Appl. No.: 16/869,466

(22) Filed: May 7, 2020

(65) Prior Publication Data
US 2020/0264156 A1    Aug. 20, 2020

Related U.S. Application Data

(63) Continuation of application No. 14/987,802, filed on Jan. 5, 2016, now abandoned.

(60) Provisional application No. 62/099,679, filed on Jan. 5, 2015.

(51) Int. Cl.
*G01N 33/28* (2006.01)
*G01N 21/3577* (2014.01)
*G01N 21/35* (2014.01)

(52) U.S. Cl.
CPC ..... *G01N 33/2823* (2013.01); *G01N 21/3577* (2013.01); *G01N 33/2841* (2013.01); *G01N 2021/3595* (2013.01)

(58) Field of Classification Search
CPC ........... G01N 33/2823; G01N 21/3577; G01N 33/2841; G01N 2021/3595
See application file for complete search history.

(56) References Cited

U.S. PATENT DOCUMENTS

| | | | | |
|---|---|---|---|---|
| 2010/0204925 A1* | 8/2010 | Albahri | ................ | G16C 20/30 702/25 |
| 2010/0305872 A1* | 12/2010 | Abahri | ................ | G01N 33/28 702/30 |
| 2015/0106031 A1* | 4/2015 | Koseoglu | ............. | G01N 21/359 702/24 |

FOREIGN PATENT DOCUMENTS

EP     0304232 A2 *  2/1989  ......... G01N 21/3577

* cited by examiner

*Primary Examiner* — Marcus H Taningco
(74) *Attorney, Agent, or Firm* — Abelman, Frayne & Schwab

(57) ABSTRACT

A system and a method are provided for calculating the cetane number, pour point, cloud point, aniline point, aromaticity, and/or octane number of a gas oil or naphtha fraction of a crude oil from the density and Fourier transform infrared spectroscopy (FTIR) of a sample of the crude oil, without first distilling the crude oil into the gas oil or naphtha fraction.

22 Claims, 4 Drawing Sheets

CHARACTERIZATION OF CRUDE OIL AND ITS FRACTIONS BY FOURIER TRANSFORM INFRARED (FTIR) SPECTROSCOPY ANALYSIS

CROSS-REFERENCE TO RELATED APPLICATION

This application is a continuation of and claims the benefit of U.S. patent application Ser. No. 14/987,802, filed Jan. 5, 2016, which claims the benefit of U.S. Provisional Patent Application No. 62/099,679 filed Jan. 5, 2015, the disclosures of which are incorporated herein by reference in its entirety.

FIELD OF THE INVENTION

This invention relates to a method and process for the evaluation of samples of crude oil and its fractions by Fourier transform infrared spectroscopy (FTIR) analysis.

BACKGROUND OF THE INVENTION

Crude oil originates from the decomposition and transformation of aquatic, mainly marine, living organisms and/or land plants that became buried under successive layers of mud and silt some 15-500 million years ago. They are essentially very complex mixtures of many thousands of different hydrocarbons. Depending on the source, the oil predominantly contains various proportions of straight and branched-chain paraffins, cycloparaffins, and naphthenic, aromatic, and polynuclear aromatic hydrocarbons. These hydrocarbons can be gaseous, liquid, or solid under normal conditions of temperature and pressure, depending on the number and arrangement of carbon atoms in the molecules.

Crude oils vary widely in their physical and chemical properties from one geographical region to another and from field to field. Crude oils are usually classified into three groups according to the nature of the hydrocarbons they contain: paraffinic, naphthenic, asphaltic, and their mixtures. The differences are due to the different proportions of the various molecular types and sizes. One crude oil can contain mostly paraffins, another mostly naphthenes. Whether paraffinic or naphthenic, one can contain a large quantity of lighter hydrocarbons and be mobile or contain dissolved gases; another can consist mainly of heavier hydrocarbons and be highly viscous, with little or no dissolved gas. Crude oils can also include heteroatoms containing sulfur, nitrogen, nickel, vanadium and other elements in quantities that impact the refinery processing of the crude oil fractions. Light crude oils or condensates can contain sulfur in concentrations as low as 0.01 W %; in contrast, heavy crude oils can contain as much as 5-6 W %. Similarly, the nitrogen content of crude oils can range from 0.001-1.0 W %.

The nature of the crude oil governs, to a certain extent, the nature of the products that can be manufactured from it and their suitability for special applications. A naphthenic crude oil will be more suitable for the production of asphaltic bitumen, a paraffinic crude oil for wax. A naphthenic crude oil, and even more so an aromatic one, will yield lubricating oils with viscosities that are sensitive to temperature. However, with modern refining methods there is greater flexibility in the use of various crude oils to produce many desired type of products.

A crude oil assay is a traditional method of determining the nature of crude oils for benchmarking purposes. Crude oils are subjected to true boiling point (TBP) distillations and fractionations to provide different boiling point fractions. The crude oil distillations are carried out using the American Standard Testing Association (ASTM) Method D 2892. The common fractions and their nominal boiling points are given in Table 1.

TABLE 1

| Fraction | Boiling Point, °C. |
| --- | --- |
| Methane | −161.5 |
| Ethane | −88.6 |
| Propane | −42.1 |
| Butanes | −6.0 |
| Light Naphtha | 36-90 |
| Mid Naphtha | 90-160 |
| Heavy Naphtha | 160-205 |
| Light gas Oil | 205-260 |
| Mid Gas Oil | 260-315 |
| Heavy gas Oil | 315-370 |
| Light Vacuum Gas Oil | 370-430 |
| Mid Vacuum Gas Oil | 430-480 |
| Heavy vacuum gas oil | 480-565 |
| Vacuum Residue | 565+ |

The yields, composition, physical and indicative properties of these crude oil fractions, where applicable, are then determined during the crude assay work-up calculations. Typical compositional and property information obtained from a crude oil assay is given in Table 2.

TABLE 2

| Property | Unit | Property Type | Fraction |
| --- | --- | --- | --- |
| Yield Weight and Volume % | W % | Yield | All |
| API Gravity | ° | Physical | All |
| Viscosity Kinematic @ 38° C. | ° | Physical | Fraction boiling >250° C. |
| Refractive Index @ 20° C. | Unitless | Physical | Fraction boiling <400° C. |
| Sulfur | W % | Composition | All |
| Mercaptan Sulfur, W % | W % | Composition | Fraction boiling <250° C. |
| Nickel | ppmw | Composition | Fraction boiling >400° C. |
| Nitrogen | ppmw | Composition | All |
| Flash Point, COC | ° C. | Indicative | All |
| Cloud Point | ° C. | Indicative | Fraction boiling >250° C. |
| Pour Point, (Upper) | ° C. | Indicative | Fraction boiling >250° C. |
| Freezing Point | ° C. | Indicative | Fraction boiling >250° C. |
| Micro Carbon Residue | W % | Indicative | Fraction boiling >300° C. |
| Smoke Point, mm | mm | Indicative | Fraction boiling between 150-250° C. |

TABLE 2-continued

| Property | Unit | Property Type | Fraction |
|---|---|---|---|
| Octane Number | Unitless | Indicative | Fraction boiling <250° C. |
| Cetane Index | Unitless | Indicative | Fraction boiling between 150-400° C. |
| Aniline Point | ° C. | Indicative | Fraction boiling <520° C. |

Due to the number of distillation cuts and the number of analyses involved, the crude oil assay work-up is both costly and time consuming.

In a typical refinery, crude oil is first fractionated in the atmospheric distillation column to separate sour gas and light hydrocarbons, including methane, ethane, propane, butanes and hydrogen sulfide, naphtha (36-180° C.), kerosene (180-240° C.), gas oil (240-370° C.) and atmospheric residue (>370° C.). The atmospheric residue from the atmospheric distillation column is either used as fuel oil or sent to a vacuum distillation unit, depending on the configuration of the refinery. The principal products obtained from vacuum distillation are vacuum gas oil, comprising hydrocarbons boiling in the range 370-520° C., and vacuum residue, comprising hydrocarbons boiling above 520° C. Crude assay data is conventionally obtained from individual analysis of these cuts to help refiners to understand the general composition of the crude oil fractions and properties so that the fractions can be processed most efficiently and effectively in an appropriate refining unit. Indicative properties are used to determine the engine/fuel performance or usability or flow characteristic or composition. A summary of the indicative properties and their determination methods with description is given below.

The cetane number of diesel fuel oil, determined by the ASTM D613 method, provides a measure of the ignition quality of diesel fuel; as determined in a standard single cylinder test engine; which measures ignition delay compared to primary reference fuels. The higher the cetane number; the easier the high-speed; direct-injection engine will start; and the less white smoking and diesel knock after start-up are. The cetane number of a diesel fuel oil is determined by comparing its combustion characteristics in a test engine with those for blends of reference fuels of known cetane number under standard operating conditions. This is accomplished using the bracketing hand wheel procedure which varies the compression ratio (hand wheel reading) for the sample and each of the two bracketing reference fuels to obtain a specific ignition delay, thus permitting interpolation of cetane number in terms of hand wheel reading.

The cloud point, determined by the ASTM D2500 method, is the temperature at which a cloud of wax crystals appears when a lubricant or distillate fuel is cooled under standard conditions. Cloud point indicates the tendency of the material to plug filters or small orifices under cold weather conditions. The specimen is cooled at a specified rate and examined periodically. The temperature at which cloud is first observed at the bottom of the test jar is recorded as the cloud point. This test method covers only petroleum products and biodiesel fuels that are transparent in 40 mm thick layers, and with a cloud point below 49° C.

The pour point of petroleum products, determined by the ASTM D97 method, is an indicator of the ability of oil or distillate fuel to flow at cold operating temperatures. It is the lowest temperature at which the fluid will flow when cooled under prescribed conditions. After preliminary heating, the sample is cooled at a specified rate and examined at intervals of 3° C. for flow characteristics. The lowest temperature at which movement of the specimen is observed is recorded as the pour point.

The aniline point, determined by the ASTM D611 method, is the lowest temperature at which equal volumes of aniline and hydrocarbon fuel or lubricant base stock are completely miscible. A measure of the aromatic content of a hydrocarbon blend is used to predict the solvency of a base stock or the cetane number of a distillate fuel. Specified volumes of aniline and sample, or aniline and sample plus n-heptane, are placed in a tube and mixed mechanically. The mixture is heated at a controlled rate until the two phases become miscible. The mixture is then cooled at a controlled rate and the temperature at which two separate phases are again formed is recorded as the aniline point or mixed aniline point.

The octane number, determined by the ASTM D2699 or D2700 methods, is a measure of a fuel's ability to prevent detonation in a spark ignition engine. Measured in a standard single-cylinder; variable-compression-ratio engine by comparison with primary reference fuels. Under mild conditions, the engine measures research octane number (RON), while under severe conditions, the engine measures motor octane number (MON). Where the law requires posting of octane numbers on dispensing pumps, the antiknock index (AKI) is used. This is the arithmetic average of RON and MON, (R+M)/2. It approximates the road octane number, which is a measure of how an average car responds to the fuel.

To determine these properties of gas oil or naphtha fractions conventionally, these fractions have to be distilled from the crude oil and then measured/identified using various analytical methods that are laborious, costly and time-consuming.

Fourier transform infrared spectroscopy (FTIR) is an analytical technique used to measure the absorbance or transmittance of light by a solid, liquid or gas sample at various wavelengths, producing an FTIR spectrum. The peaks correspond to the frequencies of vibrations of the bonds of the atoms making up the material as the sample molecules selectively absorb radiation of specific wavelengths. The FTIR spectrum represents the molecular vibrational spectrum of the sample, providing a fingerprint of the composition of the material under testing. Hence, the FTIR spectrum is characteristic of the structure of the molecule and can be used for identification (qualitative analysis). FTIR is also a good monitoring tool for chemical reactions where functional information about a specific chemical can be obtained. Since the spectrum peak size is a direct indication of the amount of the material, FTIR can also be used for quantitative analysis. The commonly used region for infrared absorption fluorescence spectroscopy is approximately 4000-400 $cm^{-1}$ because most organic compounds absorb IR radiation within this region.

This invention discloses a system and method in which FTIR analysis is employed to disclose physical and indicative properties (i.e., cetane number, pour point, cloud point, and aniline point) of gas oil fraction of crude oils, as well as the octane number of the naphtha fraction and the aromaticity of whole crude oils. The invention provides insight into the gas oil properties without fractionation/distillation (crude oil assays) and will help producers, refiners, and marketers to benchmark the oil quality and, as a result, valuate the oils without going thru costly and time consuming crude oil assays. Whereas a conventional crude oil assay method could take up to two months, this invention provides results within one hour.

New rapid, and direct methods to help better understand crude oil compositions and properties from analysis of whole crude oil will save producers, marketers, refiners and/or other crude oil users substantial expense, effort and time. Therefore, a need exists for an improved system and method for determining indicative properties of crude oil fractions from different sources.

SUMMARY OF THE INVENTION

Systems and methods for determining one or more indicative properties of a hydrocarbon sample are presented. Indicative properties in a crude oil sample (e.g., cetane number, pour point, cloud point and aniline point) of a gas oil fraction, octane number of a naphtha fraction, and the aromaticity for the whole crude oil (WCO), are assigned as a function of density and FTIR measurement of a crude oil sample. The indicative properties provide information about the gas oil and naphtha properties without fractionation/distillation (crude oil assays) and help producers, refiners, and marketers to benchmark the oil quality and, as a result, valuate the oils without performing the customary extensive and time-consuming crude oil assays.

BRIEF DESCRIPTION OF THE DRAWINGS

Further advantages and features of the present invention will become apparent from the following detailed description of the invention when considered with reference to the accompanying drawings in which.

DETAILED DESCRIPTION OF INVENTION

A system and a method are provided for determining one or more indicative properties of a hydrocarbon sample. Indicative properties (e.g., cetane number, pour point, cloud point, and aniline point) of a gas oil fraction and ozone number of a naphtha fraction in a crude oil sample are assigned as a function of the density and FTIR measurement of the crude oil sample. The indicative properties provide information about the gas oil and naphtha properties without fractionation/distillation (crude oil assays) and help producers, refiners, and marketers to benchmark the oil quality and, as a result, valuate the oils without performing the customary extensive and time-consuming crude oil assays.

The systems and methods are applicable for naturally occurring hydrocarbons derived from crude oils, bitumens, heavy oils, shale oils and from refinery process units including hydrotreating, hydroprocessing, fluid catalytic cracking, coking, and visbreaking or coal liquefaction.

In the system and method herein, FTIR analysis is obtained by a suitable known or to-be-developed process. Fourier transform infrared spectroscopy uses an FTIR spectrophotometer to simultaneously collect spectral data of a solid, liquid, or gas over a wide spectral range. A Fourier transform is employed to convert the raw data into the actual spectrum. The method confers a significant advantage over a dispersive spectrophotometer that measures intensity over a narrow range of wavelengths at a time.

In one embodiment, a Varian 660-IR (FTIR) spectrophotometer equipped with a Specac's Golden Gate ATR accessory with a diamond crystal was used for the analysis of the crude oil. The background FTIR run was taken against a clean accessory. For sample analysis, three drops of crude oil were placed on the diamond crystal and the crystal was covered with a plastic cap to minimize sample evaporation. The instrument was then scanned over the wavelength range from 4000-700 $CM^{-1}$.

Figure 1:
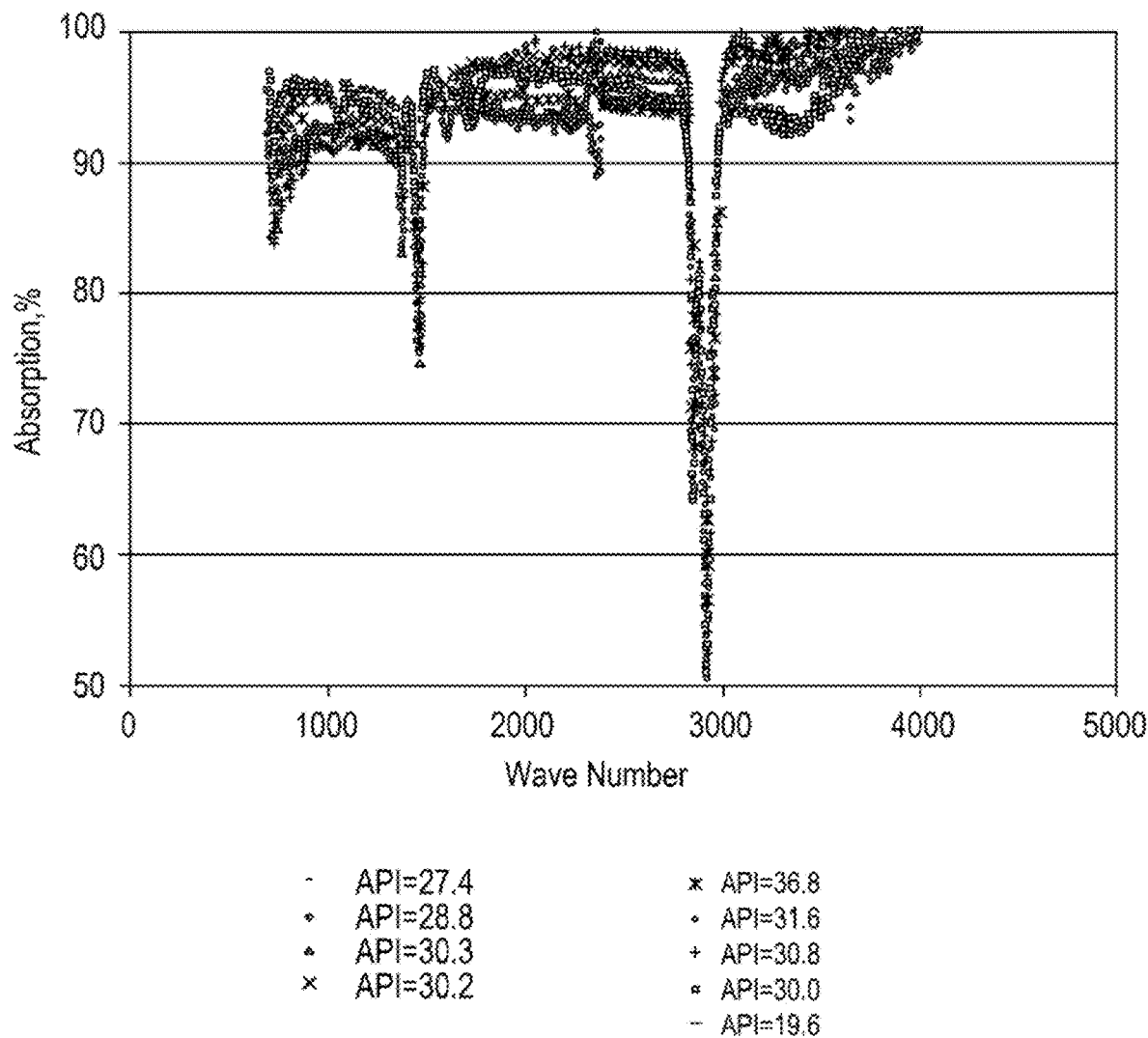
FIG. 1 is a graphic plot of typical FTIR data for typical crude oil samples with different API gravities.

Typical Fourier transform infrared spectroscopy data for crude oils with different API gravities are shown in FIG. 1.

In one embodiment, the FTIR index is calculated as follows. The maximum transmittances (maxtrans) are determined for each of a number of crude oils under investigation.

$$FTIRI_{desired\ crude} = maxtrans_{desired\ crude} - maxtrans_{lowest\ value} \quad (1);$$

Figure 2:
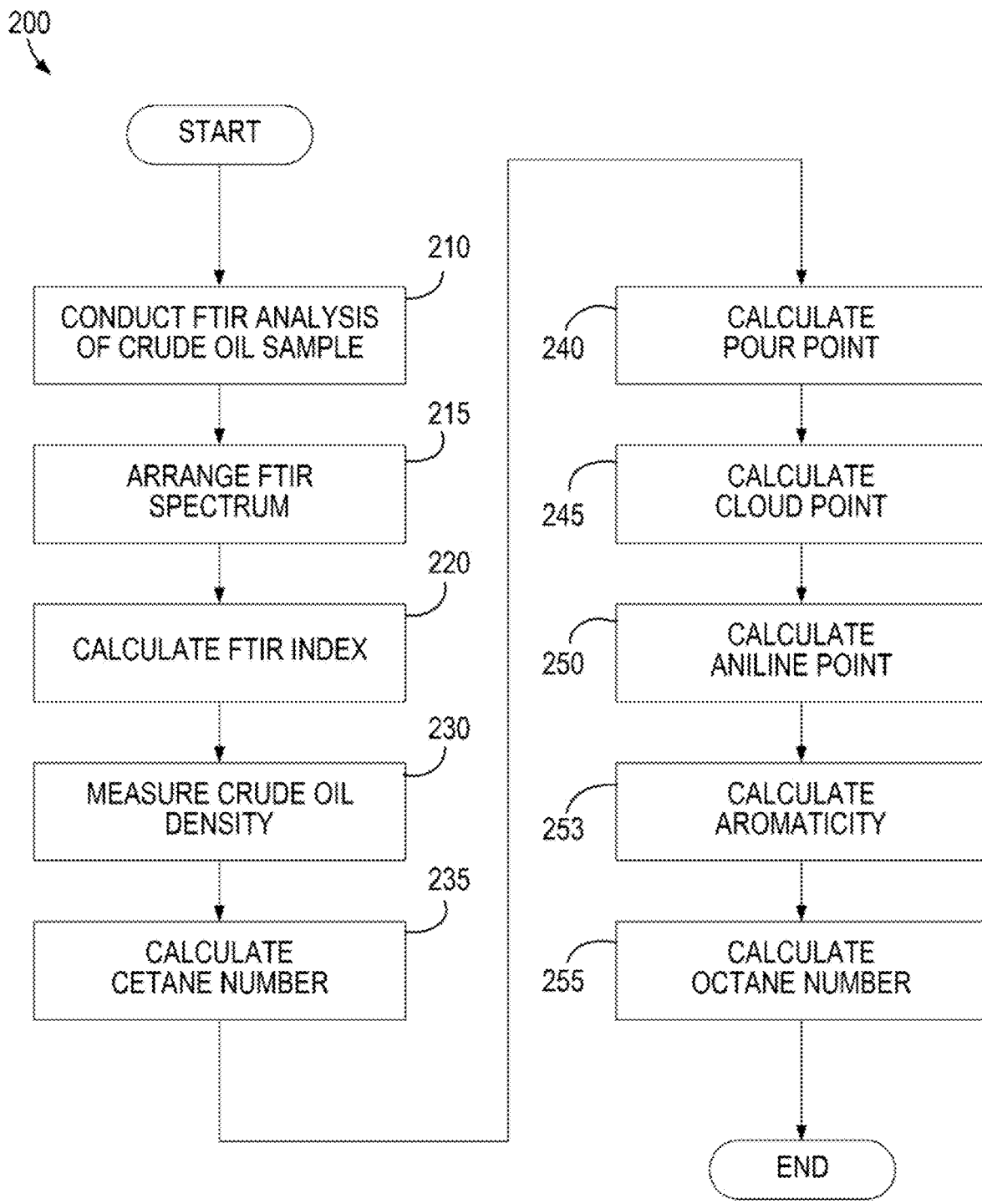
FIG. 2 is a block diagram of a method in which an embodiment of the invention is implemented.

FIG. 2 shows a process flowchart of steps in a method according to one embodiment herein, in which crude oil samples are prepared and analyzed by FTIR according to the method 200 described below.

In step 210 a sample of three drops of crude oil is placed via a pipette on the diamond crystal and the crystal was covered with a plastic cap to minimize sample evaporation. No sample dilution or special sample preparation is required. The instrument was then scanned over the wavelength range from 4000-700 $CM^{-1}$.

In step 215, the FTIR data is arranged so that maximum transmittances are determined.

In step 220, an FTIR index (FTIRI) is calculated according to equation (1).

The indicative properties (e.g., the cetane number, pour point, cloud point and aniline point) of the gas oil fraction, e.g. boiling in the range of 150–400° C. and in certain embodiments in the range of 180–370° C., the octane number of the naphtha fraction, and the aromaticity for the whole crude oil (WCO), can be assigned as a function of the density and the FTIRI of crude oil. That is, $$Indicative\ Property = f(density_{crude\ oil}, FTIRI_{crudeoil}) \quad (2);$$

Equation (3) is a detailed example of this relationship, showing the cetane number, pour point, cloud point and aniline point that can be predicted for the gas oil (GO) fraction of the crude oil, as well as the aromaticity that can be predicted for the whole crude oil (WCO), as well as the octane number that can be predicted for the naphtha fraction.

In steps 235, 240, 245, and 250, respectively, the properties of a cetane number, pour point, cloud point and aniline point for the gas oil (GO) fraction of the crude oil are calculated, in step 253 the aromaticity for the whole crude oil (WCO) is calculated, and in step 255 the property of an octane number for the naphtha fraction of the crude oil is calculated. While FIG. 2 shows the steps performed sequentially, they can be performed in parallel or in any order. In certain embodiments, only one or more steps 235, 240, 245, 250, 253, 255 are carried out. In these steps, the one or more indicative properties are determined as follows:

$$\text{Indicative property} = K + X1*DEN + X2*DEN^2 + X3*DEN^3 + X4*\text{FTIRI} + X5*\text{FTIRI}^2 + X6*\text{FTIRI}^3 + X7*DEN*\text{FTIRI} \quad (3);$$

where:

DEN=density of the crude oil sample; and

K, X1-X7, are constants for the properties to be predicted that are developed using linear regression analysis of hydrocarbon data from FTIR.

Figure 3:
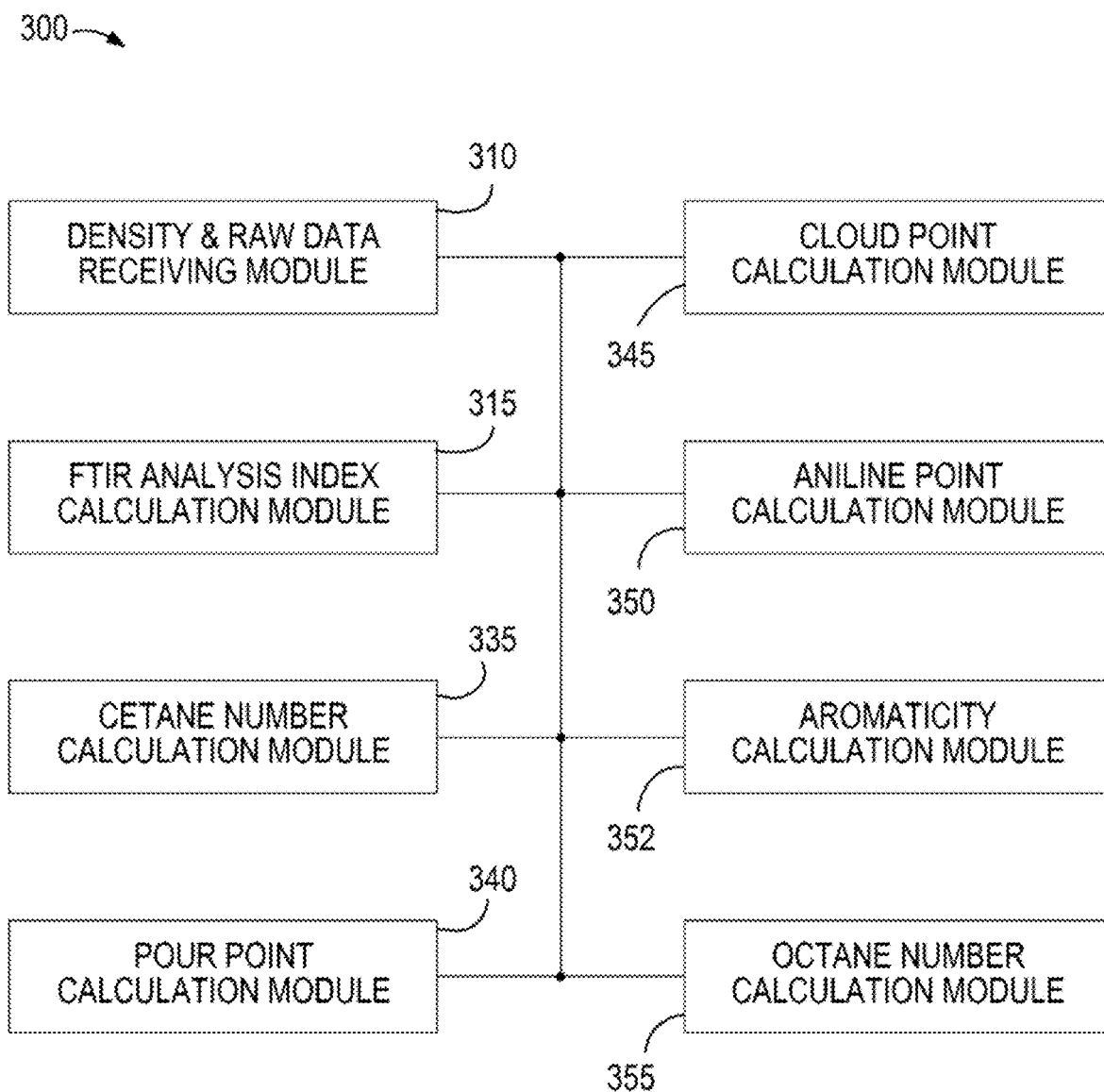
FIG. 3 is a schematic block diagram of modules of an embodiment of the invention.

FIG. 3 illustrates a schematic block diagram of modules in accordance with an embodiment of the present invention, system 300. Density and raw data receiving module 310 receives the density of a sample of crude oil and Fourier transform infrared fluorescence spectroscopy data derived from the crude oil.

FTIR index calculation module 315 calculates the Fourier transform infrared spectroscopy index from the FTIR data.

Cetane number calculation module 335 derives the cetane number for the gas oil fraction of the crude oil as a function of the Fourier transform infrared spectroscopy index and density of the sample.

Pour point calculation module 340 derives the pour point for the gas oil fraction of the crude oil as a function of the Fourier transform infrared spectroscopy index and density of the sample.

Cloud point calculation module 345 derives the cloud point for the gas oil fraction of the crude oil as a function of the Fourier transform infrared spectroscopy index and density of the sample.

Aniline point calculation module 350 derives the aniline point for the gas oil fraction of the crude oil as a function of the Fourier transform infrared spectroscopy index and density of the sample.

Aromaticity calculation module 352 derives the aromaticity for the whole crude oil as a function of the Fourier transform infrared spectroscopy index and density of the sample.

Octane number calculation module 355 derives the octane number for the naphtha fraction of the crude oil as a function of the Fourier transform infrared spectroscopy index and density of the sample.

Figure 4:
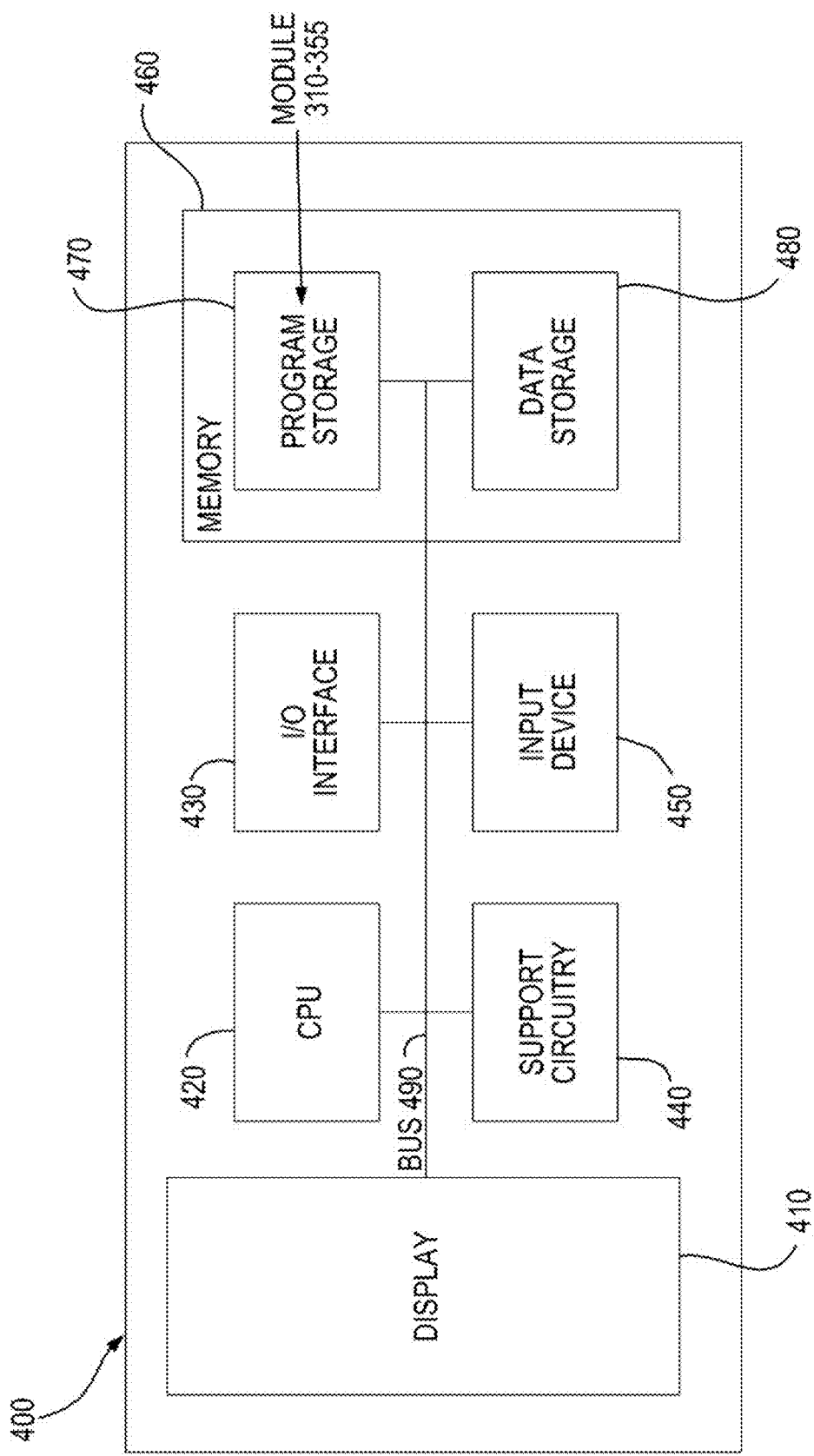
FIG. 4 is a block diagram of a computer system in which an embodiment of the invention is implemented.

FIG. 4 shows an exemplary block diagram of a computer system 400 in which one embodiment of the present invention can be implemented. Computer system 400 includes a processor 420, such as a central processing unit, an input/output interface 430 and support circuitry 440. In certain embodiments, where the computer system 400 requires a direct human interface, a display 410 and an input device 450 such as a keyboard, mouse or pointer are also provided. The display 410, input device 450, processor 420, and support circuitry 440 are shown connected to a bus 490 which also connects to a memory 460. Memory 460 includes program storage memory 470 and data storage memory 480. Note that while computer system 400 is depicted with direct human interface components display 410 and input device 450, programming of modules and exportation of data can alternatively be accomplished over the input/output interface 430, for instance, where the computer system 400 is connected to a network and the programming and display operations occur on another associated computer, or via a detachable input device as is known with respect to interfacing programmable logic controllers.

Program storage memory 470 and data storage memory 480 can each comprise volatile (RAM) and non-volatile (ROM) memory units and can also comprise hard disk and backup storage capacity, and both program storage memory 470 and data storage memory 480 can be embodied in a single memory device or separated in plural memory devices. Program storage memory 470 stores software program modules and associated data, and in particular stores a density and raw data receiving module 310, Fourier transform infrared spectroscopy index calculation module 315, cetane number calculation module 335, pour point calculation module 340, cloud point calculation module 345, aniline point calculation module 350, aromaticity calculation module 352, and octane number calculation module 355. Data storage memory 480 stores results and other data generated by the one or more modules of the present invention.

It is to be appreciated that the computer system 400 can be any computer such as a personal computer, minicomputer, workstation, mainframe, a dedicated controller such as a programmable logic controller, or a combination thereof. While the computer system 400 is shown, for illustration purposes, as a single computer unit, the system can comprise a group of computers which can be scaled depending on the processing load and database size.

Computer system 400 preferably supports an operating system, for example stored in program storage memory 470 and executed by the processor 420 from volatile memory. According to an embodiment of the invention, the operating system contains instructions for interfacing computer system 400 to the Internet and/or to private networks.

Example 1

A set of constants K and X1-X7 was determined using linear regression for the indicative properties cetane number, pour point, cloud point, aniline point, octane number, and aromaticity. These constants were determined based on known actual distillation data for plural crude oil samples and their corresponding indicative properties. These constants are given in Table 3.

TABLE 3

| Constants | Cetane Number | Pour Point | Cloud Point | Aniline Point |
|---|---|---|---|---|
| K | 1.353576E+05 | 1.099007E+05 | 5.550384E+04 | 7.717846E+04 |
| X1 | −4.652678E+05 | −3.752190E+05 | −1.896601E+05 | −2.654884E+05 |
| X2 | 5.312307E+05 | 4.267904E+05 | 2.162203E+05 | 3.033093E+05 |
| X3 | −2.013982E+05 | −1.617556E+05 | −8.225676E+04 | −1.149909E+05 |
| X4 | 1.946958E+02 | 2.197450E+01 | −1.600659E+01 | 1.402683E+02 |
| X5 | −3.773736E+00 | −1.151301E+00 | −7.195605E−02 | −2.699202E+00 |
| X6 | 1.955737E−01 | 5.885146E−02 | 4.288102E−03 | 1.364182E−01 |
| X7 | −2.042985E+02 | −1.901277E+01 | 1.848965E+01 | −1.466497E+02 |

| Constants | Octane Number | WCO-AROM |
|---|---|---|
| K | 8.202192E+05 | −2.937030E+04 |
| X1 | −2.845858E+06 | 1.041119E+05 |

TABLE 3-continued

| | | |
|---|---|---|
| X2 | 3.290683E+06 | −1.218370E+05 |
| X3 | −1.268002E+06 | 4.713092E+04 |
| X4 | −1.182558E+01 | −6.655481E+01 |
| X5 | 2.582860E+00 | −6.705168E−01 |
| X6 | −1.277980E−01 | 3.361324E−02 |
| X7 | 0.0000000E+00 | 7.911532E+01 |

The following example is provided to demonstrate an application of equations (3). A sample of Arabian medium crude with a 15° C./4° C. density of 0.8828 Kg/l was analyzed by FTIR, using the described method. The tabulated results follow in Table 4:

TABLE 4

| Crude Oils WL, cm$^{-1}$ | API = 28.8° Transmission, % | API = 19.6° Transmission, % |
|---|---|---|
| 700 | 97.38 | 95.14 |
| 720 | 93.42 | 94.27 |
| 740 | 93.87 | 91.75 |
| 760 | 95.20 | 94.14 |
| 780 | 96.86 | 94.52 |
| 800 | 96.81 | 93.76 |
| 820 | 97.04 | 93.86 |
| 840 | 98.72 | 95.07 |
| 860 | 98.88 | 95.04 |
| 880 | 98.18 | 94.73 |
| 900 | 99.89 | 95.96 |
| 920 | 99.89 | 96.65 |
| 940 | 100.72 | 96.08 |
| 960 | 100.26 | 96.58 |
| 980 | 100.36 | 96.30 |
| 1000 | 100.40 | 96.62 |
| 1020 | 99.95 | 96.95 |
| 1040 | 99.92 | 96.54 |
| 1060 | 100.11 | 96.72 |
| 1080 | 100.47 | 96.77 |
| 1100 | 100.56 | 97.24 |
| 1120 | 100.74 | 97.09 |
| 1140 | 100.14 | 97.01 |
| 1160 | 99.74 | 96.42 |
| 1180 | 100.50 | 96.60 |
| 1200 | 100.73 | 96.92 |
| 1220 | 100.88 | 96.24 |
| 1240 | 99.95 | 96.16 |
| 1260 | 100.24 | 96.20 |
| 1280 | 99.62 | 95.67 |
| 1300 | 99.35 | 95.46 |
| 1320 | 99.34 | 95.52 |
| 1340 | 99.51 | 95.05 |
| 1360 | 98.34 | 93.83 |
| 1380 | 92.60 | 88.37 |
| 1400 | 100.42 | 96.27 |
| 1420 | 100.41 | 95.22 |
| 1440 | 92.28 | 87.02 |
| 1460 | 83.72 | 79.45 |
| 1480 | 98.74 | 94.53 |
| 1500 | 101.28 | 97.10 |
| 1520 | 104.46 | 98.58 |
| 1540 | 105.33 | 98.85 |
| 1560 | 104.49 | 98.59 |
| 1580 | 101.55 | 97.60 |
| 1600 | 100.85 | 96.54 |
| 1620 | 102.64 | 97.44 |
| 1640 | 102.65 | 98.14 |
| 1660 | 102.91 | 98.54 |
| 1680 | 103.58 | 98.80 |
| 1700 | 104.79 | 98.97 |
| 1720 | 103.61 | 99.16 |
| 1740 | 103.36 | 99.25 |
| 1760 | 102.80 | 99.27 |
| 1780 | 103.07 | 99.52 |
| 1800 | 103.25 | 99.50 |
| 1820 | 102.39 | 99.49 |
| 1840 | 102.49 | 99.37 |
| 1860 | 102.40 | 99.52 |
| 1880 | 102.12 | 99.43 |
| 1900 | 102.29 | 99.28 |
| 1920 | 102.88 | 99.65 |
| 1940 | 102.53 | 99.64 |
| 1960 | 102.07 | 99.50 |
| 1980 | 102.72 | 99.58 |
| 2000 | 102.27 | 99.08 |
| 2020 | 102.38 | 99.63 |
| 2040 | 102.98 | 99.95 |
| 2060 | 102.03 | 99.41 |
| 2080 | 102.45 | 99.29 |
| 2100 | 102.08 | 99.12 |
| 2120 | 102.54 | 99.13 |
| 2140 | 102.68 | 99.74 |
| 2160 | 102.07 | 99.99 |
| 2180 | 102.55 | 99.17 |
| 2200 | 101.50 | 99.74 |
| 2220 | 103.54 | 98.91 |
| 2240 | 102.41 | 99.26 |
| 2260 | 102.41 | 99.77 |
| 2280 | 102.08 | 99.34 |
| 2300 | 102.58 | 99.11 |
| 2320 | 105.38 | 99.28 |
| 2340 | 106.71 | 99.76 |
| 2360 | 108.80 | 99.58 |
| 2380 | 103.61 | 99.44 |
| 2400 | 102.07 | 99.09 |
| 2420 | 102.35 | 99.09 |
| 2440 | 102.22 | 99.08 |
| 2460 | 101.84 | 99.00 |
| 2480 | 102.23 | 99.11 |
| 2500 | 101.78 | 99.43 |
| 2520 | 101.85 | 98.76 |
| 2540 | 102.28 | 99.18 |
| 2560 | 102.03 | 98.94 |
| 2580 | 101.85 | 99.16 |
| 2600 | 102.04 | 98.94 |
| 2620 | 102.00 | 98.83 |
| 2640 | 101.71 | 98.64 |
| 2660 | 101.56 | 98.73 |
| 2680 | 101.46 | 98.43 |
| 2700 | 101.45 | 98.89 |
| 2720 | 101.28 | 98.09 |
| 2740 | 101.53 | 98.48 |
| 2760 | 101.64 | 98.65 |
| 2780 | 101.77 | 98.47 |
| 2800 | 101.00 | 97.70 |
| 2820 | 99.78 | 95.76 |
| 2840 | 88.18 | 83.12 |
| 2860 | 76.69 | 73.72 |
| 2880 | 86.13 | 81.10 |
| 2900 | 76.59 | 71.62 |
| 2920 | 56.50 | 56.75 |
| 2940 | 78.17 | 72.96 |
| 2960 | 80.38 | 77.30 |
| 2980 | 97.61 | 93.36 |
| 3000 | 101.06 | 97.51 |
| 3020 | 101.07 | 97.58 |
| 3040 | 101.22 | 98.28 |
| 3060 | 102.62 | 99.05 |
| 3080 | 102.20 | 99.12 |
| 3100 | 101.82 | 98.70 |
| 3120 | 102.30 | 98.86 |
| 3140 | 102.85 | 98.91 |

TABLE 4-continued

| Crude Oils WL, cm$^{-1}$ | API = 28.8° Transmission, % | API = 19.6° Transmission, % |
|---|---|---|
| 3160 | 102.85 | 97.72 |
| 3180 | 103.05 | 99.53 |
| 3200 | 103.77 | 99.32 |
| 3220 | 102.97 | 100.13 |
| 3240 | 103.45 | 99.20 |
| 3260 | 103.39 | 99.53 |
| 3280 | 103.04 | 98.35 |
| 3300 | 102.86 | 99.59 |
| 3320 | 102.41 | 99.93 |
| 3340 | 102.48 | 99.45 |
| 3360 | 102.25 | 98.99 |
| 3380 | 103.11 | 99.48 |
| 3400 | 103.62 | 99.49 |
| 3420 | 102.99 | 99.70 |
| 3440 | 103.46 | 99.99 |
| 3460 | 102.48 | 99.40 |
| 3480 | 103.48 | 99.28 |
| 3500 | 103.29 | 99.63 |
| 3520 | 103.65 | 99.14 |
| 3540 | 103.55 | 99.24 |
| 3560 | 102.41 | 98.82 |
| 3580 | 104.15 | 99.61 |
| 3600 | 105.09 | 99.50 |
| 3620 | 104.65 | 99.43 |
| 3640 | 103.48 | 99.72 |
| 3660 | 103.25 | 100.49 |
| 3680 | 102.93 | 99.85 |
| 3700 | 103.40 | 99.81 |
| 3720 | 103.49 | 98.98 |
| 3740 | 104.42 | 99.77 |
| 3760 | 103.62 | 99.76 |
| 3780 | 103.66 | 99.61 |
| 3800 | 104.76 | 99.75 |
| 3820 | 104.37 | 100.06 |
| 3840 | 103.63 | 99.56 |
| 3860 | 103.66 | 99.58 |
| 3880 | 103.76 | 99.70 |
| 3900 | 103.83 | 99.77 |
| 3920 | 102.74 | 99.49 |
| 3940 | 102.52 | 99.57 |
| 3960 | 102.40 | 99.92 |
| 3980 | 102.11 | 99.59 |
| 4000 | 102.09 | 99.61 |

As noted in equation (1), FTIRI is calculated by comparing the maximum transmittances for a number of crude oils under investigation. In the example above, for a crude oil designated "AM," the maximum transmittance maxtrans$_{AM}$=108.797. The minimum value of these maximum transmittances is that for the crude oil designated "IHI," for which maxtrans$_{IHI}$=94.935.

Similar FTIR data was obtained for a number of other oils, with the maximum transmittances shown in Table 5, below. As can be seen, the lowest of the maximum transmittance is found for the oil designated "IHI," which has a maximum transmittance of 94.935.

TABLE 5

|  | AM | AH | L1 | SSL | XSL | UR | BI | IHI | MB |
|---|---|---|---|---|---|---|---|---|---|
| API Gravity, ° | 28.8 | 27.4 | 30.3 | 30.2 | 36.8 | 31.6 | 30.8 | 30.0 | 19.6 |
| maxtrans | 108.797 | 101.530 | 100.691 | 102.154 | 105.794 | 107.708 | 108.144 | 94.935 | 101.448 |
| FTIRI | 13.862 | 6.595 | 5.756 | 7.219 | 10.858 | 12.773 | 13.209 | 0.000 | 6.512 |

Applying equation (1), FTIRI for the oil "AM" under investigation was calculated to be:

FTIRI=[maxtrans$_{AM}$]−[min-of-maxtrans], so FTIRI for AM Crude is [108.797]−[94.935]=13.862

Applying equation (3) and the constants from Table 3:

$$\begin{aligned}
\text{Cetane Number}_{GO}\ (CET) =\ & K_{CET} + X1_{CET} * DEN + \\
& X2_{CET} * DEN^2 + X3_{CET} * \\
& DEN^3 + X4_{CET} * FTIRI + \\
& X5_{CET} * FTIRI^2 + X6_{CET} * \\
& FTIRI^3 + X7_{CET} * DEN * FTIRI \\
=\ & (1.353576E + 05) + \\
& (-4.652678E + 05)(0.8828) + \\
& (5.312307E + 05)(0.8828)^2 + \\
& (-2.013982E + 05)(0.8828)^3 + \\
& (1.946958E + 02)(13.862) + \\
& (-3.773736E + 00)(13.862)^2 + \\
& (1.955737E - 01)(13.862)^3 + \\
& (-2.042985E + 02)(0.8828)(13.862) \\
=\ & 59
\end{aligned}$$

$$\begin{aligned}
\text{Pour Point}_{GO}\ (PP) =\ & K_{PP} + X1_{PP} * DEN + X2_{PP} * DEN^2 + \\
& X3_{PP} * DEN^3 + X4_{PP} * FTIRI + \\
& X5_{PP} * FTIRI^2 + X6_{PP} * FTIRI^3 + \\
& X7_{PP} * DEN * FTIRI \\
=\ & (1.099007E + 05) + \\
& (-3.752190E + 05)(0.8828) + \\
& (4.267904E + 05)(0.8828)^2 + \\
& (-1.617556E + 05)(0.8828)^3 + \\
& (2.197450E + 01)(13.862) + \\
& (-1.151301E + 00)(13.862)^2 + \\
& (5.885146E - 02)(13.862)^3 + \\
& (-1.901277E + 01)(0.8828)(13.862) \\
=\ & -10
\end{aligned}$$

$$\begin{aligned}\text{Cloud Point}_{GO}\ (CP) =\ & K_{CP} + X1_{CP}*DEN + X2_{CP}*DEN^2 + \\ & X3_{CP}*DEN^3 + X4_{CP}*FTIRI + \\ & X5_{CP}*FTIRI^2 + X6_{CP}*FTIRI^3 + \\ & X7_{CP}*DEN*FTIRI \\ =\ & (5.550384E+04) + \\ & (-1.896601E+05)(0.8828) + \\ & (2.162203E+05)(0.8828)^2 + \\ & (-0.8225676E+04)(0.8828)^3 + \\ & (-1.600659E+05)(13.862) + \\ & (-7.195605E-02)(13.862)^2 + \\ & (4.288102E-03)(13.862)^3 + \\ & (1.848965E+01)(0.8828)(13.862) \\ =\ & -10 \end{aligned}$$

$$\begin{aligned}\text{Aniline Point}_{GO}\ (AP) =\ & K_{AP} + X1_{AP}*DEN + X2_{AP}*DEN^2 + \\ & X3_{AP}*DEN^3 + X4_{AP}*FTIRI + \\ & X5_{AP}*FTIRI^2 + X6_{AP}*FTIRI^3 + \\ & X7_{AP}*DEN*FTIRI \\ =\ & (7.717846E+04) + \\ & (-2.654884E+05)(0.8828) + \\ & (3.033093E+05)(0.8828)^2 + \\ & (-1.149909E+05)(0.8828)^3 + \\ & (1.402683E+02)(13.862) + \\ & (-2.699202E+00)(13.862)^2 + \\ & (1.364182E-01)(13.862)^3 + \\ & (-1.466497E+02)(0.8828)(13.862) \\ =\ & 66 \end{aligned}$$

$$\begin{aligned}\text{Aromaticity}_{WCO}\ (AROM) =\ & K_{AROM} + X1_{AROM}*DEN + X2_{AROM}* \\ & DEN^2 + X3_{AROM}*DEN^3 + X4_{AROM}* \\ & FTIRI + X5_{AROM}*FTIRI^2 + \\ & X6_{AROM}*FTIRI^3 + X7_{AROM}*DEN* \\ & FTIRI \\ =\ & (-2.937030E+04) + \\ & (1.041119E+05)(0.8828) + \\ & (-1.218370E+05)(0.8828)^2 + \\ & (4.713092E+04)(0.8828)^3 + \\ & (-6.655481E+01)(13.862) + \\ & (-6.705168E-01)(13.862)^2 + \\ & (3.361324E-02)(13.862)^3 + \\ & (7.911532E+01)(0.8828)(13.862) \\ =\ & 20 \end{aligned}$$

$$\begin{aligned}\text{Octane Number}\ (ON) =\ & K_{ON} + X1_{ON}*DEN + X2_{ON}*DEN^2 + \\ & X3_{ON}*DEN^3 + X4_{ON}*FTIRI + \\ & X5_{ON}*FTIRI^2 + X6_{ON}*FTIRI^3 + \\ & X7_{ON}*DEN*FTIRI \\ =\ & (8.202192E+05) + \\ & (-2.845858E+06)(0.8828) + \\ & (3.290683E+06)(0.8828)^2 + \\ & (-1.268002E+06)(0.8828)^3 + \\ & (-1.182558E+01)(13.862) + \\ & (2.582860E+00)(13.862)^2 + \\ & (-1.277980E-01)(13.862)^3 + \\ & (0)(0.8828)(13.862) \\ =\ & 52 \end{aligned}$$

Accordingly, as shown in the above example, indicative properties including cetane number, pour point, cloud point, aniline point, and aromaticity can be assigned to the crude oil samples without fractionation/distillation (crude oil assays).

In alternate embodiments, the present invention can be implemented as a computer program product for use with a computerized computing system. Those skilled in the art will readily appreciate that programs defining the functions of the present invention can be written in any appropriate programming language and delivered to a computer in any form, including but not limited to: (a) information permanently stored on non-writeable storage media (e.g., read-only memory devices such as ROMs or CD-ROM disks); (b) information alterably stored on writeable storage media (e.g., floppy disks and hard drives); and/or (c) information conveyed to a computer through communication media, such as a local area network, a telephone network, or a public network such as the Internet. When carrying computer readable instructions that implement the present invention methods, such computer readable media represent alternate embodiments of the present invention.

As generally illustrated herein, the system embodiments can incorporate a variety of computer readable media that comprise a computer usable medium having computer readable code means embodied therein. One skilled in the art will recognize that the software associated with the various processes described can be embodied in a wide variety of computer accessible media from which the software is loaded and activated. Pursuant to In re Beauregard, 35 U.S.P.Q.2d 1383 (U.S. Pat. No. 5,710,578), the present invention contemplates and includes this type of computer readable media within the scope of the invention. In certain embodiments, pursuant to In re Nuijten, 500 F.3d 1346 (Fed. Cir. 2007) (U.S. patent application Ser. No. 09/211,928), the scope of the present claims is limited to computer readable media, wherein the media is both tangible and non-transitory.

The system and method of the present invention have been described above and with reference to the attached figures; however, modifications will be apparent to those of ordinary skill in the art and the scope of protection for the invention is to be defined by the claims that follow.

We claim:

1. A system for evaluating a crude oil sample and calculating at least one indicative property of a naphtha or gas oil fraction of the crude oil sample without first distilling said naphtha or gas oil fraction, wherein the at least one indicative property is selected from cetane number, pour point, cloud point, aniline point, aromaticity, and octane number, the system comprising:
- a non-volatile memory device that stores calculation modules and data, wherein the calculation modules include at least a first calculation module and a second calculation module, and wherein the data includes density of the crude oil sample and Fourier transform infrared spectroscopy data derived by an analysis of the crude oil sample by a Fourier transform infrared spectrophotometer, wherein the spectroscopic data is indicative of transmittance values at predetermined increments between a predetermined range for the crude oil sample; and
- a processor coupled to the non-volatile memory;
- wherein the first calculation module, upon being executed by the processor, retrieves the Fourier transform infrared spectroscopy data from the non-volatile memory, that calculates a crude oil Fourier transform infrared spectroscopy index value of the fraction from the transmittance values of the spectroscopy data, and that transfers the calculated Fourier transform infrared spectroscopy index into the non-volatile memory; and
- wherein the second calculation module, upon being executed by the processor, calculates the at least one indicative property for the fraction of the crude oil from a two-variable polynomial equation with predetermined constant coefficients developed using linear regression techniques, and stores the at least one indicative property into the non-volatile memory device;
- wherein the two variables of the two-variable polynomial equation are the Fourier transform infrared spectroscopy index and the density of the crude oil sample.

2. The system of claim 1, wherein the indicative property is the cetane number.

3. The system of claim 1, wherein the indicative property is the pour point.

4. The system of claim 1, wherein the indicative property is the cloud point.

5. The system of claim 1, wherein the indicative property is the aniline point.

6. The system of claim 1, wherein the indicative property is the aromaticity.

7. The system of claim 1, wherein the indicative property is the octane number.

8. The system of claim 1, wherein the spectroscopic data is derived by a Fourier transform infrared spectrophotometer with a temperature range of 20-80° C.

9. The system of claim 1, wherein the Fourier transform infrared spectroscopy index is that of whole crude oil.

10. The system of claim 1, wherein the Fourier transform infrared spectroscopy index is calculated from FTIR data measured in the wavelength range of 700-4000 cm$^{-1}$.

11. The system of claim 1, wherein the Fourier transform infrared spectroscopy data is obtained directly from core and/or drill cuttings material.

12. A method for evaluating a crude oil sample and calculating at least one indicative property of a naphtha or gas oil fraction of the crude oil sample without first distilling said naphtha or gas oil fraction, wherein the at least one indicative property is selected from cetane number, pour point, cloud point, aniline point, aromaticity, and octane number, the method comprising;
- receiving the density of the crude oil sample and storing it into non-volatile memory of a computer;
- receiving Fourier transform infrared spectroscopic data derived by an analysis of the crude oil sample by a spectrophotometer, wherein the spectroscopic data is indicative of transmittance values at predetermined increments between a predetermined range for the oil sample, and storing the spectroscopic data into the non-volatile memory;
- using a processor of the computer that is coupled to the non-volatile memory to calculate a crude oil Fourier transform infrared spectroscopy index value of fraction from the transmittance values; and
- using the processor to calculate and record into the non-volatile memory the at least one indicative property for the naphtha or gas oil fraction of the crude oil from a two-variable polynomial equation with predetermined constant coefficients developed using linear regression techniques;
- wherein the two variables of the two-variable polynomial equation are the Fourier transform infrared spectroscopy index and the density of the crude oil sample.

13. The method of claim 12, wherein the indicative property is the cetane number.

14. The method of claim 12, wherein the indicative property is the pour point.

15. The method of claim 12, wherein the indicative property is the cloud point.

16. The method of claim 12, wherein the indicative property is the aniline point.

17. The method of claim 12, wherein the indicative property is the aromaticity.

18. The method of claim 12, wherein the indicative property is the octane number.

19. The method of claim 12, wherein the spectroscopic data is derived by a Fourier transform infrared spectrophotometer with a temperature range of 20-80° C.

20. The method of claim 12, wherein the Fourier transform infrared spectroscopy index is that of whole crude oil.

21. The method of claim 12, wherein the Fourier transform infrared spectroscopy index is calculated from FTIR data measured in the wavelength range of 700-4000 cm$^{-1}$.

22. The method of claim 12, wherein the Fourier transform infrared spectroscopy data is obtained directly from core and/or drill cuttings material.

* * * * *